(12) United States Patent
Stihl

(10) Patent No.: US 6,877,672 B2
(45) Date of Patent: Apr. 12, 2005

(54) METHOD AND DISPENSER FOR MIXING AND DISCHARGING MEDIA

(75) Inventor: Alexander Stihl, Radolfzell (DE)

(73) Assignee: Ing. Erich Pfeiffer GmbH, Radolfzell (DE)

(*) Notice: Subject to any disclaimer, the term of this patent is extended or adjusted under 35 U.S.C. 154(b) by 0 days.

(21) Appl. No.: 10/327,770

(22) Filed: Dec. 23, 2002

(65) Prior Publication Data

US 2003/0127533 A1 Jul. 10, 2003

(30) Foreign Application Priority Data

Dec. 21, 2001 (DE) .......................... 101 64 452

(51) Int. Cl.⁷ ................................ A62C 5/02
(52) U.S. Cl. ............................ 239/8; 222/82
(58) Field of Search .................. 239/8, 272, 309; 222/82, 83, 321.6, 141.1

(56) References Cited

U.S. PATENT DOCUMENTS

| | | | |
|---|---|---|---|
| 2,151,418 A | 5/1937 | Bolte | |
| 2,754,590 A | 7/1956 | Cohen | |
| 5,349,947 A | 9/1994 | Newhouse et al. | |
| 5,366,122 A | 11/1994 | Geuntert et al. | |
| 5,683,361 A * | 11/1997 | Elk et al. | 604/58 |
| 5,810,004 A | 9/1998 | Ohki et al. | |
| 5,967,369 A | 10/1999 | Käfer et al. | |
| 6,065,641 A * | 5/2000 | Laguna Valderrama | 222/80 |
| 6,179,164 B1 | 1/2001 | Fuchs | |
| 6,398,074 B1 | 6/2002 | Bruna et al. | |
| 2002/0023641 A1 | 2/2002 | Stadelhofer | |
| 2002/0056760 A1 * | 5/2002 | Piper | 239/8 |

FOREIGN PATENT DOCUMENTS

| | | |
|---|---|---|
| DE | 3416083 | 10/1985 |
| DE | 4400084 | 7/1995 |
| DE | 19502725 | 8/1996 |
| DE | 19708406 | 9/1998 |
| EP | 1186312 | 3/2002 |
| WO | 9946055 | 9/1999 |

* cited by examiner

Primary Examiner—Thomas Denion
Assistant Examiner—Zelalem Eshete
(74) Attorney, Agent, or Firm—D. Peter Hochberg; Sean Mellino; Katherine R. Vieyra

(57) ABSTRACT

The object of the invention is to provide a method and a dispenser in which, compared with known dispensers, the fluid path design is simplified. The dispenser has a medium reservoir (19) containing a medium to be discharge during one discharge stroke of the dispenser (11). For this purpose a feed fluid flows through the medium reservoir and discharges the medium through a reservoir discharge opening. For producing a discharge stroke, the dispenser has an actuator (25), whose actuation at least indirectly leads to an impact spike (29) penetrating from the outside into the medium reservoir (19), so as to produce a connection between a pump (40) for a feed fluid and the medium reservoir. As a result of the pressure of the feed fluid flowing into the medium reservoir, at a point in the medium reservoir (19) differing from the entry point of the impact spike (29), an opening is formed.

14 Claims, 3 Drawing Sheets

METHOD AND DISPENSER FOR MIXING AND DISCHARGING MEDIA

BACKGROUND OF THE INVENTION

The invention relates to a method and to a dispenser for mixing and discharging a medium mixture mixed from two media.

DE 19817417 A (corresponding to U.S. Ser. No. 09/554031) discloses a dispenser, in which a medium to be discharged, e.g. a powder, is received in a blister ring. The user operates an air pump cylinder and presses the blister ring against a hollow impact spike, which perforates a cover foil of a blister chamber. Through said opening, air enters the blister chamber and discharges the medium through the hollow impact spike. Thus, the air enters the medium chamber alongside or through the impact spike and passes out from the same again. This limits the line cross-section and the flow guidance for a good mixing.

OBJECT OF THE INVENTION

An object of the invention is to provide a method and dispenser simplifying the guidance of the media, which reduces the requirement for easy miscibility of the media and which improves the mixing process.

SUMMARY OF THE INVENTION

As defined in claim 1, the invention provides a method in which a first medium, e.g. a feed or delivery fluid, is delivered from a first chamber on operating the dispenser into an initially closed, second chamber on opening the latter, e.g. through an impact spike. Thus, the pressurized first medium enters the second chamber and places the same under media pressure, which brings about the opening of the second chamber. This can take place by the bursting of a wall of the second chamber, e.g. the cover foil of a blister, whose body is pierced from below by the impact spike. Said wall part can be prepared by material weakening, e.g. in the form of a predetermined breaking point. However, it is also possible for the discharge closure element of the second chamber to also be pierced in order to assist the opening under media pressure. The second chamber can also have a displaceable wall part, e.g. a plug, which is perforated, blown off or obviated by a bypass, if media pressure from the second chamber acts thereon.

In all cases the media path is simplified, because the flow through the second chamber can take place without any significant deflection, i.e. a straight passage is created. Nevertheless the mixing of the two media is good, because the feed fluid enters in planned manner and as a result of the pressure build-up in the second chamber a certain mixing time is also available and this can contribute to the second medium dissolving in the first medium, e.g. a powder in a liquid.

The second medium can be in liquid or solid form, particularly as a powder. It can then be mixed with the first medium, which can be mainly gaseous (air) or liquid and as a result all possible mixture forms or dispersions between the same can form, particularly aerosols with liquid or solid particles, emulsions, solutions or suspensions, as well as foams. In the pharmaceutical sector this is particularly important, e.g. for lyophilizates. Many pharmaceutical substances, which usually form the second medium, are not stable in the liquid or pulverulent administration form, so that they can only be mixed or dissolved just prior to administration. The pharmaceutical substances are often lyophilized powders. However, pharmaceutical substances are often absorbable or surface-active via the nasal mucosa. The feed fluid (first medium) can also contain pharmaceutical substances or can react chemically or physically with the second medium for forming the ultimate pharmaceutical substance.

If the discharge closure element is constituted by a foil, the material thickness in the region of the weakening can be minimized to approximately 9 to 12 $\mu$m and is therefore smaller than the wall thickness of the remaining foil. Use is more particularly made of metal foils, e.g. aluminium foils. As such weakened points contain no definition of the start of the breaking point, when designing the foil it must be ensured that there is a continuous, propagating tearing open of the foil starting at a specific point in order to e.g. avoid a detonation effect. This could e.g. be brought about by a laser perforation of the material, which can also be guided along the entire predetermined breaking point. Perforation is performed in such a way that also in this area the material remains tight with respect to fluids and gas exchange.

Additionally or alternatively to material weakening, in the vicinity of the surface portion to be broken open, the impact spike can pierce or perforate the medium reservoir and this precisely defines the position of the start of tearing open.

Advantageously, the second chamber (medium reservoir) can at least be zonally deformable. As a result even in the case of changing external pressures, there is scarcely a pressure difference between atmosphere and the interior of, in particular, the second chamber, which keeps limited the fusion and gas exchange with the atmosphere. As a result, the material thicknesses of the medium reservoir wall can be kept small.

In the advantageous use of a blister, the latter usually comprises a moulding, which is e.g. cup or bowl-shaped with an edge and which is closed by a foil material. The latter can be a metal foil, a metal vapour-deposited plastic foil or film or a multilayer foil or film formed from laminates. The choice of the foil material determines the "damming" i.e. the size of the pressure build-up prior to the pressure-caused opening of the discharge closure element. This must be made sufficiently high to ensure that the outflowing media mixture has or can reach the desired use form. In the case of a discharge in the form of a spray through a spraying nozzle, a relatively high initial pressure should be present.

According to another embodiment, the medium reservoir has a plug axially displaceably arranged about a movement path. As a result of the axial displacement, the fluid path between the medium reservoir and the discharge opening is freed and this takes place under the pressure rise in the second chamber.

The second chamber can be replaceable. Thus, a dispenser can be reloaded for repeated use. It is also possible through manual operation to place the feed fluid in the first chamber initially under a pressure without initiating the overflow into the first chamber. Then, at high speed and corresponding advantages for the mixing process, it passes into the second chamber. In addition, the feed fluid need only be compressed just prior to its discharge and need not be stored for a long time in a pressure-tight reservoir, although this is also possible.

These and further features can be gathered from the claims, description and drawings and the individual features, both singly or in the form of subcombinations, can be implemented in an embodiment of the invention and in other fields and can represent advantageous, independently protectable constructions for which protection is claimed here. The subdivision of the application into individual sections and the subheadings in no way limit the general nature of the statements made thereunder.

BRIEF DESCRIPTION OF THE DRAWINGS

Embodiments of the invention are shown in the attached drawings, wherein show.

DESCRIPTION OF PREFERRED EMBODIMENTS

Figure 1:
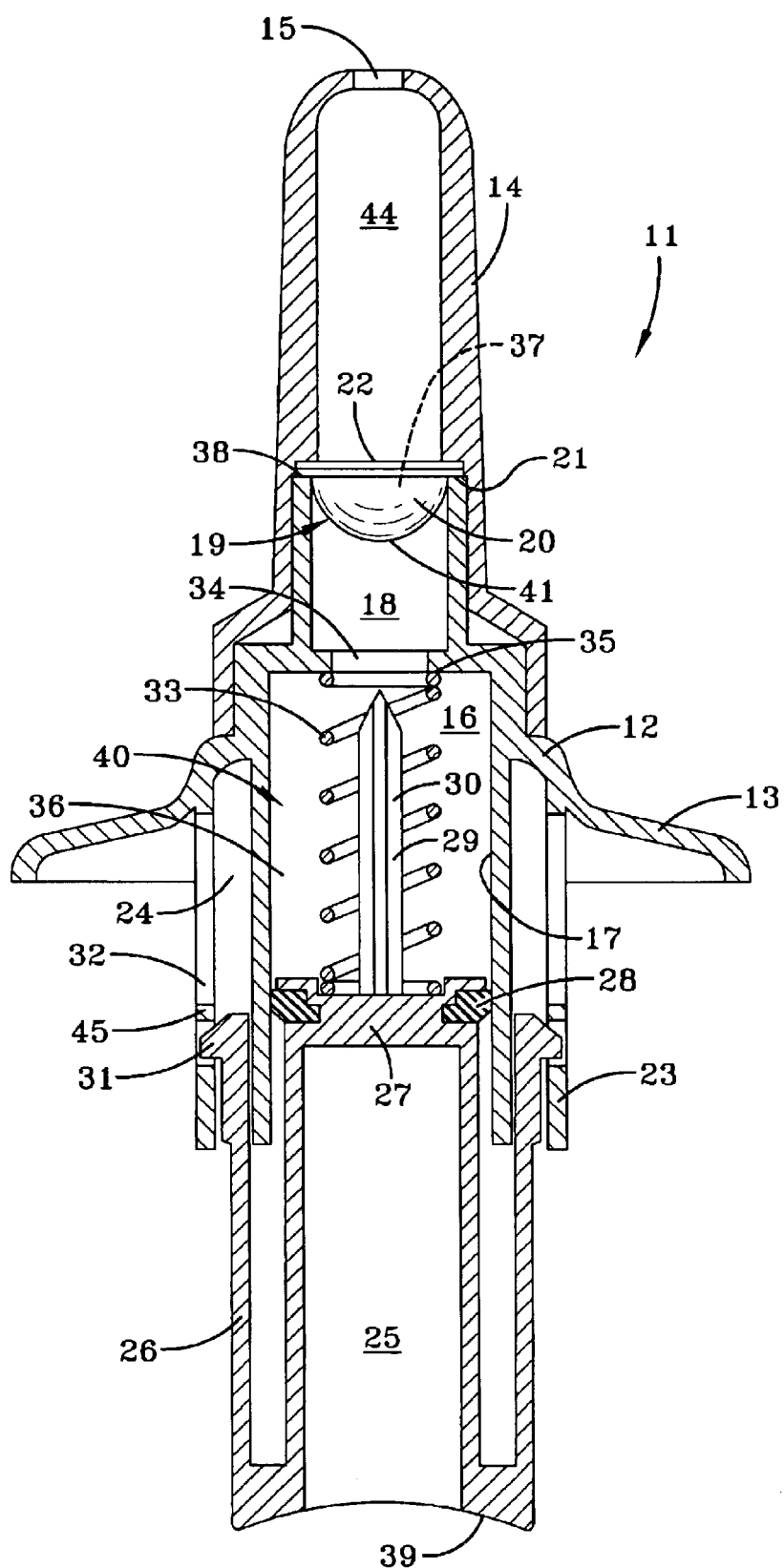
FIG. 1 A diagrammatic longitudinal section through a dispenser for performing the method according to the invention.

FIG. 1 shows a dispenser 11 with a base body 12, which has laterally projecting shoulders 13 on which are placed two fingers of a user. Onto the base body 12 can be engaged or screwed an elongated adaptor 14, also known as a nose olive and which has at its rounded end a discharge opening 15. The latter is shown as a relatively large, open hole, but when constructing the dispenser as an atomizer, it can also contain an atomizing nozzle.

The base body 12 contains a first chamber 16, which has a cylindrical section 17 constructed as a pump cylinder and a section 18 connected thereto. At the end thereof is interchangeably inserted a second chamber 19 and is held there by the adaptor. The second chamber comprises a blister with a hemispherical, bowl-shaped plastic moulding 20 and an edge 21, onto which is sealed a discharge closure element 22 in the form of a metal foil or plastic film tightly sealing the second chamber. The blister is fixed at the edge 21 in tight manner between an upper end face of the base part and the adaptor.

The cylinder 17 of the base part 12 is surrounded by a slightly expandable jacket 23. In the intermediately formed annular clearance 24 is guided an actuator 25 having cylindrical or web-like guide parts 26. Between the latter, the actuator contains a piston 27, which runs by means of an inserted or also shaped-on seal 28 in the cylinder 17. On the piston head is placed or shaped an impact spike 29, which by a ribbed structure, e.g. a cruciform cross-section, forms overflow channels 30 in the manner to be described hereinafter.

At their ends the guide parts or arms 26 of the actuator 25 have detents 31, which run in guide slots 32 of the jacket 23 and prevent the actuator 25 from detaching itself from the base part 12 following initial snapping in.

A restoring spring 33 is located in the cylinder 17 and embraces the impact spike 29, being supported on shoulders 35 surrounding the connecting opening 34 between cylinder 17 and the following section 18. It can be a steel helical spring or a plastic spring optionally pointed on the piston 27. In this case all the parts of the dispenser would be made from plastic, which permits type-pure recycling.

The first chamber contains a first medium 36, which is a feed or delivery fluid, e.g. a liquid or gas such as air. The second chamber (blister 19) forms a medium reservoir for a second medium 37, e.g. pulverulent pharmaceutical substances.

The dispenser is used for performing the following method:

In preparation for administration, a user places a blister 19 in the dispenser by removing or unscrewing the adaptor 14, places the blister on the end face 38 of base part 12 and refits the adaptor. The cylinder 17 is then filled with air, which in this case forms the feed fluid 36. If the user now places two fingers on the shoulders 13 and presses with the thumb on the actuating surface 39 on actuator 25, he can press the latter upwards and therefore compress the air in the pump 40 formed by cylinder 17 and piston 27. This takes place until the impact spike 29 strikes against the moulding 20 of the blister 19 and perforates the same (cf. FIG. 3).

Figure 3:
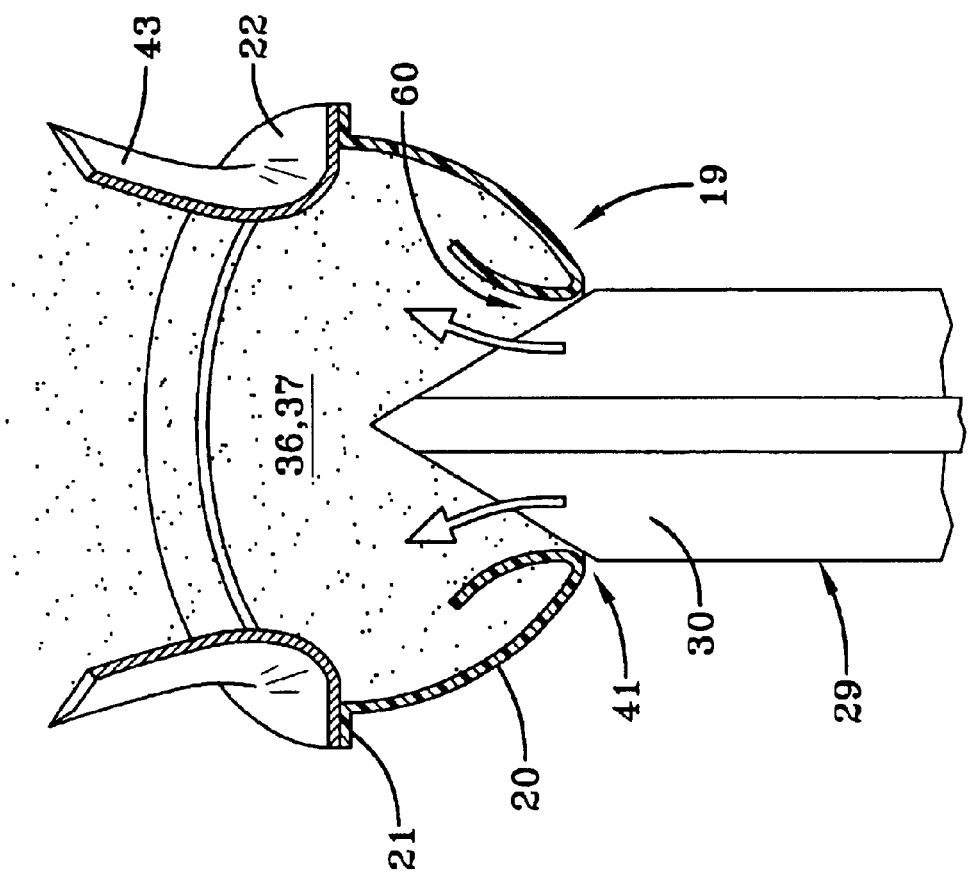
FIGS. 2 & 3 Medium reservoirs (second chambers) in two successive method stages.

FIG. 3 shows in a perspective sectional representation that the bottom of the moulding of the blister has been perforated by an overflow closure element 41. As a result of the cruciform structure of the impact spike 29, in the vicinity of the overflow channels 30 an opening 60 is formed through which the now compressed air enters the blister and places the latter under pressure.

Figure 2:
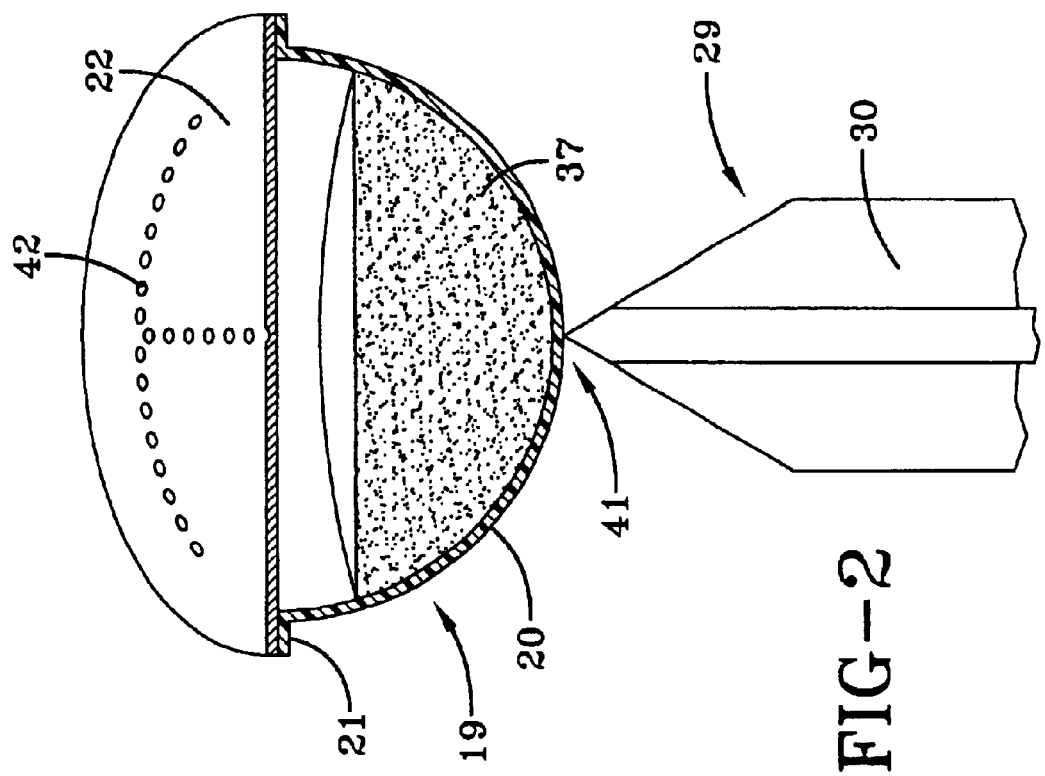

FIG. 2 shows that the blister has material weakenings 42 on its sealed-on foil forming the discharge closure element 22 and said weakenings are e.g. in the form of a scoring, embossing or non-continuous laser perforation, which in the example shown is in the form of a rounded off H. Under the media pressure in the blister the foil is therefore torn open along said material weakening and is e.g. folded out into two lateral tongues 43 or into four tongues in the case of an X-shaped material weakening. Thus, the foil is burst by the internal pressure, the feed fluid 36 flows under its pressure through the blister, carries with it the second medium 37 by mixing therewith in order to form a solid aerosol. Through the space 44 formed in the adaptor, the mixture flows to the discharge opening 15 and at the desired point where it has been placed by the user it is e.g. applied to a nostril.

In place of the planned material weakening at certain points, these can also be provided in the form of lines or points, this being carried out by the foil manufacturer prior to blister processing. There is also a formation of a mechanical preweakening, which gives rise to a predetermined breaking point. This contributes to allowing the blister to "explode" so as to bring about a sudden whirling up of the substance in the second chamber, but it is necessary to avoid a detonation, which might frighten the user, by a clearly defined tearing open direction, i.e. a more pronounced material weakening at one point and a following reduced "propagating" weakening.

It is also possible to constructionally combine the blister with the adaptor 14, so that said unit can be replaced for further actuation. This ensures that there is also a replacement of the adaptor part possibly coming into contact with body fluid.

It is also pointed out that prior to the start of actuation the actuator must overcome a pressure point, which would be formed by the web 45 in slot 32. The web can be located in fixed manner, so that the detent 31 with its bevel and the widening of the jacket, which can optionally be made elastic by elongated slots, produces the pressure point. The webs 45 can also be break-off webs provided with predetermined breaking points, which produce a precisely predetermined resistance. Thus, even before the start of use, a slight force expenditure is demanded of the user and ensures that actuation is not too timorous and therefore not particularly effective. However, due to the fact that the opening of the overflow closure element 41 (blister bottom) only takes place after producing the pressure in the first chamber, from then on an automatic control is created ensuring a reliable discharge. Even following the perforation of the blister bottom, the piston can optionally be forced further in the discharge direction and can thereby score a foil forming the discharge closure element 22 for the case that the foil has not been torn open solely by air pressure. It then tears open suddenly and in large-area form, so that its opening and therefore the discharge of the second medium takes place through a very large opening.

The operation of the pump has tensioned the restoring spring 33 and returns the actuator 25 and therefore the pump piston 27 to the initial position sucking air into the pump. By removing the adaptor 14 and replacing the blister 19 by an unused blister, the dispenser is again ready for use. In the case where it is a disposable dispenser, there is no need for the spring 33.

The relationship of the pump stroke volume to a dead volume in section 18, including the volume of the second chamber 19, determines the pressure, which should exceed the predetermined bursting pressure of the discharge closure element 22.

Figure 4:
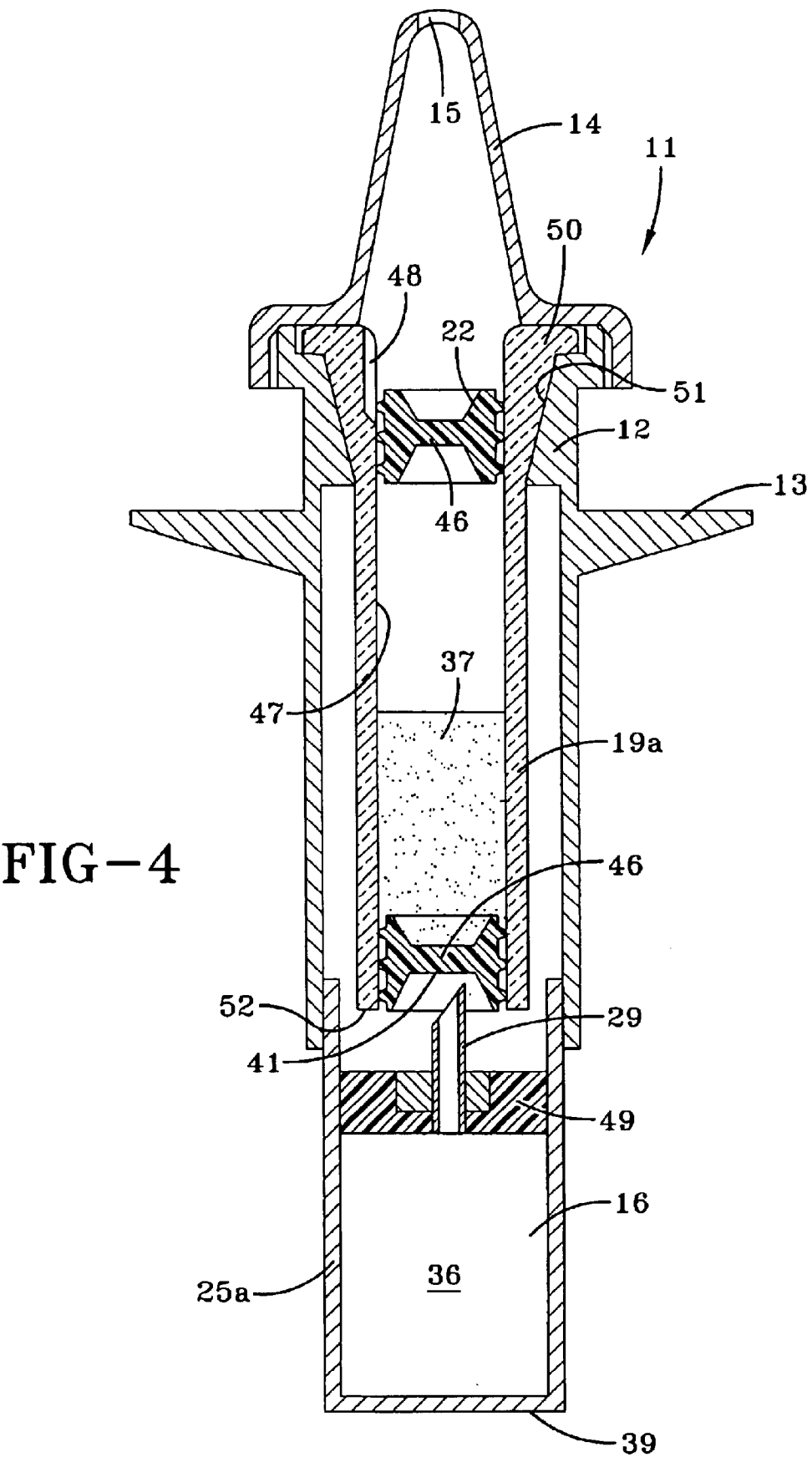
FIG. 4 A longitudinal section through a further dispenser for performing the method.

FIG. 4 shows a dispenser, whose base body 12 with shoulders 13 receives an e.g. glass cylinder 19a, which forms the second chamber and contains the second medium 37. The cylinder 19a is bilaterally closed by, in each case, a piston plug, whereof the lower plug in FIG. 4 forms the overflow closure element 41 and the upper plug forms the discharge closure element 22. The piston plugs have an H-shaped longitudinal section with a thinner, central bar 46, which can form a perforating membrane, particularly in the case of the overflow closure element 41. They run with sealing lips on the cylinder inner face of the second chamber 19a. In the vicinity of the discharge closure element 22 it has an overflow channel or bypass 48, which in the represented inoperative state is closed towards the second chamber by the discharge closure element 22.

The base body 12 guides a sleeve-like actuator 25a forming in its interior the first chamber 16 and containing the first medium 36. The first chamber is bounded by a piston 49, in whose centre is inserted, by means of a bushing, an impact spike 29 in the form of a hollow needle.

The adaptor 14 also present in this embodiment is screwed onto the upper end of the base part 12 and fixes in an upper flange 50 of the first chamber 19 and presses it into a conical receptacle 51 in the base part.

The method of operation is similar to that described hereinbefore:

When pressure is exerted on the actuating face 39 of actuator 25a, the latter is moved into the base part 12. The impact spike 29 perforates the web 46 of the overflow closure element 41 and opens the same. The lower end face 52 of the second chamber 19a strikes the piston 49 and presses it downwards, so that the feed fluid 36 flows through the hollow needle 29 into the second chamber 19a and mixes with the second medium 37. If the pressure in said chamber is sufficiently high for the upper piston forming the discharge closure element 22 to be displaced further upwards, the discharge closure is opened, namely by the bypass 48. Here again the internal pressure in the second chamber 19a brings about the opening of the discharge closure. The resulting mixture then flows in a substantially linear manner through the second chamber 19a to the discharge opening 15. In this construction the first chamber 16 is open to the atmosphere. If the feed fluid 36 is air, this does not represent a problem.

What is claimed is:

1. Method for discharging a medium mixture mixed from a first and a second medium (36, 37) through a discharge opening (15) of a dispenser (11) having a first chamber (16) containing the first medium (36);

a second chamber (19, 19a) containing the second medium (37), said second chamber having a discharge closure element (22) for the second chamber, connected to the discharge opening (15);

a media connecting path between the chambers, said path being initially closed; and at least one overflow closure element (41) for the media connecting path, wherein after opening the overflow connecting element the first medium (36) is caused to flow into the second chamber (19, 19a), thereby mixing the first and second medium to create a pressurized media mixture and as a result of the media pressure of the media mixture in the second chamber (19), opening the discharge closure element (22), the discharge closure element (22) including a material weakening (42), including a predetermined breaking point, a reduced material thickness and a laser perforation in a wall of the second chamber (19), the material weakening being initiated by piercing the wall by means of an impact spike (29).

2. Method according to claim 1, wherein the opening of the overflow closure element (41) is brought about by exerting pressure on the first chamber.

3. Method for discharging a medium mixture mixed from a first and a second medium (36, 37) through a discharge opening (15) of a dispenser (11) having a first chamber (16) containing the first medium (36);

a second chamber (19, 19a) containing the second medium (37), said second chamber having a discharge closure element (22) connected to the discharge opening (15), the discharge closure element being a breakable wall;

a media connecting path between the chambers, said path being initially closed; and at least one overflow closure element (41) for the media connecting path, wherein after opening the overflow connecting element the first medium (36) is caused to flow into the second chamber (19, 19a), thereby mixing the first and second medium to create a pressurized media mixture and wherein an impact spike (29) is used to open the overflow closure element (41) and thereafter also to initiate opening of the discharge closure element (22) as a result of piercing the wall with the spike and of bursting due to the media pressure of the media mixture in the second chamber.

4. Method according to claim 3, wherein the discharge closure element is opened by displacement of a closure member.

5. Dispenser for discharging a media mixture mixed from a first and a second medium (36, 37) through a discharge opening (15) of a dispenser (11), said dispenser comprising:

an air pump to be operated by an actuator (25), a first chamber (16) containing the first medium (36), a second chamber (19, 19a) containing the second medium (37), a media connecting path between the chambers, said path being closed by an overflow closure element (41) and discharge closure element (22), for the second chamber (19, 19a), connected to the discharge opening (15), an impact spike (29) connected to and moveable with the actuator to pierce the overflow closure element (41) and subsequently initiate by piercing the discharge closure element (22) to open as a result of the piercing and of media pressure in the second chamber (19, 19a).

6. Dispenser according to claim 5, wherein the second chamber (19, 19a) is enclosed by a blister with a moulding (20) and a foil sealing the second chamber.

7. Dispenser for discharging a media mixture mixed from a first and a second medium (36, 37) through a discharge opening (15) of a dispenser (11) comprising a first chamber (16) containing the first medium (36), a second chamber (19, 19a) containing the second medium (37), a media connecting path between the chambers, said path being closed by an overflow closure element (41) and a discharge closure element (22), for the second chamber (19, 19a), connected to the discharge opening (15), the discharge closure element (22) being constructed so as to open as a result of media pressure in the second chamber (19, 19a), the discharge closure element having an axially displaceable closure body, openable by an overflow channel (48) bypassing the closure body.

8. Dispenser according to claim 5, wherein the second chamber (19a) is constructed as a substantially cylindrical body bilaterally closed by a plug-like closure body, one closure body forming the discharge closure element (22) and the other closure body (41) is perforatable by means of said impact spike (29).

9. Dispenser according to claim 5, wherein the second chamber (19) is replaceably received in the dispenser (11).

10. Dispenser for discharging a dispersion of a powder in air, comprising:
a manually operateable piston pump containing the air in a pump chamber;
a pump piston guided in the pump chamber provided to be shifted by hand;
a blister containing the powder in a bowl-shaped body, closed by a foil sealed to a rim of the bowl-shaped body;
the blister being held in a dispenser body in a movement path of a spike moveable together with an operating stroke of the piston thereby piercing the bowl-shaped body of the blister and opening it to the pump chamber, allowing the air to flow into the blister, mixing air and powder to create the dispersion and pressurizing the dispersion;
the blister being replaceably, but—during operation of the dispenser—fixedly received in the dispenser;
the foil being breakable under pressure of the pressurized dispersion; and
an outlet opening of the dispenser body.

11. Dispense according to claim 10, wherein the dispenser body has at least two parts and wherein said dispenser further comprises a rim between the at least two parts, the blister being fixed at said rim.

12. Dispenser according to claim 5, wherein the second chamber (19) is replaceably received in the dispenser (11).

13. Dispense according to claim 6, wherein the second chamber (19) is replaceably received in the dispenser (11).

14. Dispense according to claim 7, wherein the second chamber (19) is replaceably received in the dispenser (11).

* * * * *